(12) United States Patent
Arbab et al.

(10) Patent No.: US 9,295,402 B1
(45) Date of Patent: Mar. 29, 2016

(54) METHODS AND SYSTEMS FOR ASSESSING A BURN INJURY

(71) Applicant: University of Washington through its Center for Commercialization, Seattle, WA (US)

(72) Inventors: Mohammad Hassan Arbab, Seattle, WA (US); Pierre D. Mourad, Seattle, WA (US); Antao Chen, Lake Forest Park, WA (US); Trevor C. Dickey, Durham, NC (US); Matthew D. Klein, Seattle, WA (US); Dale P. Winebrenner, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 295 days.

(21) Appl. No.: 13/744,259

(22) Filed: Jan. 17, 2013

Related U.S. Application Data

(60) Provisional application No. 61/587,179, filed on Jan. 17, 2012.

(51) Int. Cl.
*A61B 5/05* (2006.01)
*A61B 5/00* (2006.01)
*G01B 9/02* (2006.01)
*G01N 21/3581* (2014.01)
*G01N 21/3586* (2014.01)

(52) U.S. Cl.
CPC ............ *A61B 5/0507* (2013.01); *A61B 5/0075* (2013.01); *A61B 5/445* (2013.01); *G01B 9/02072* (2013.04); *G01N 21/3581* (2013.01); *G01N 21/3586* (2013.01)

(58) Field of Classification Search
CPC .... A61B 5/0507; A61B 5/0075; A61B 5/445; G01B 9/02072; G01N 21/3581; G01N 21/3586
See application file for complete search history.

(56) References Cited

U.S. PATENT DOCUMENTS

| | | | |
|---|---|---|---|
| 6,078,047 A * | 6/2000 | Mittleman et al. | 250/338.1 |
| 7,087,902 B2 * | 8/2006 | Wang et al. | 250/341.1 |
| 7,307,258 B2 * | 12/2007 | Tao et al. | 250/341.1 |
| 2010/0069758 A1 * | 3/2010 | Barnes et al. | 600/473 |
| 2012/0191371 A1 * | 7/2012 | Arbab et al. | 702/28 |
| 2013/0130237 A1 * | 5/2013 | Ouchi | 435/6.1 |

OTHER PUBLICATIONS

Arbab et al., "Application of wavelet transforms in terahertz spectroscopy of rough surface targets", Proc. of SPIE vol. 7601, Terahertz Technology and Applications III, 760106, 2010.*
E. Mandelcom, M. Gomez and R. C. Cartotto, "Work-related burn injuries in Ontario, Canada: Has anything changed in the last 10 years?," Burns 29 (5), 469-472 (2003).
B. S. Atiyeh, S. W. Gunn and S. N. Hayek, "State of the art in burn treatment," World J. Surg. 29 (2), 131-148 (2005).
J. M. Still, E. J. Law, K. G. Klavuhn, T. C. Island and J. Z. Holtz, "Diagnosis of burn depth using laser-induced Indocyanine green fluorescence: A preliminary clinical trial," Burns 27 (4), 364-371 (2001).

(Continued)

*Primary Examiner* — Long V Le
*Assistant Examiner* — Colin T Sakamoto
(74) *Attorney, Agent, or Firm* — McDonnell Boehnen Hulbert & Berghoff LLP

(57) ABSTRACT

The present invention provides methods, software, and systems for assessing a burn injury.

18 Claims, 7 Drawing Sheets

(56) References Cited

OTHER PUBLICATIONS

P. Shakespeare, "Burn wound healing and skin substitutes," Burns 27 (5), 517-522 (2001).

M. A. Afromowitz, J. B. Callis, D. M. Heimbach, L. A. DeSoto and M. K. Norton, "Multispectral imaging of burn wounds: A new clinical instrument for evaluating burn depth," IEEE Trans. Biomed. Eng. 35 (10), 842-850 (1988).

H. A. Green, D. Bua, R. R. Anderson and N. S. Nishioka, "Burn depth estimation using Indocyanine green fluorescence," Arch. Dermatol. 128 (1), 43-49 (1992).

M. J. Koruda, A. Zimbler, R. G. Settle, D. O. Jacobs, R. H. Rolandelli, G. L. Wolf and J. L. Rombeau, "Assessing burn wound depth using in vitro nuclear magnetic resonance (NMR)," J. Surg. Res. 40 (5), 475-481 (1986).

S. Iraniha, M. E. Cinat, V. M. VanderKam, A. Boyko, D. Lee, J. Jones and B. M. Achauer, "Determination of burn depth with noncontact ultrasonography," J. Burn Care Res. 21 (4), 333-338 (2000).

A. Papp, T. Lahtinen, M. Harma, J. Nuutinen, A. Uusaro and E. Alhava, "Dielectric Measurement in Experimental Burns: A New Tool for Burn Depth Determination?," Plast. Reconstr. Surg. 117 (3), 889-898 (2006).

A. D. Jaskille, J. C. Ramella-Roman, J. W. Shupp, M. H. Jordan and J. C. Jeng, "Critical review of burn depth assessment techniques: part II. Review of laser Doppler technology," J. Burn Care Res. 31(1), 151-157 (2010).

S. M. Srinivas, J. F. Boer, H. Park, K. Keikhanzadeh, H.-e. L. Huang, J. Zhang, W. Q. Jung, Z. Chen and J. S. Nelson, "Determination of burn depth by polarization-sensitive optical coherence tomography," J. Biomed. Opt. 9 (1), 207-212 (2004).

M. G. Sowa, L. Leonardi, J. R. Payette, K. M. Cross, M. Gomez and J. S. Fish, "Classification of burn injuries using near-infrared spectroscopy," J. Biomed. Opt. 11 (5), 054002 (2006).

K. M. Cross, L. Leonardi, J. R. Payette, M. Gomez, M. A. Levasseur, B. J. Schattka, M. G. Sowa and J. S. Fish, "Clinical utilization of near-infrared spectroscopy devices for burn depth assessment," Wound Repair Regen. 15 (3), 332-340 (2007).

P. H. Siegel, "Terahertz technology in biology and medicine," IEEE Trans. Microw. Theory Tech. 52 (10), 2438-2447 (2004).

E. Pickwell and V. P. Wallace, "Biomedical applications of terahertz technology," J. Phys. D Appl. Phys. 39 (17), R301 (2006).

D. B. Bennett, Z. D. Taylor, P. Tewari, R. S. Singh, M. O. Culjat, W. S. Grundfest, D. J. Sassoon, R. D. Johnson, J.-P. Hubschman and E. R. Brown, "Terahertz sensing in corneal tissues," J. Biomed. Opt. 16 (5), 057003 (2011).

Z. D. Taylor, R. S. Singh, D. B. Bennett, P. Tewari, C. P. Kealey, N. Bajwa, M. O. Culjat, A. Stojadinovic, L. Hua, J. P. Hubschman, E. R. Brown and W. S. Grundfest, "THz medical imaging: In vivo hydration sensing," IEEE Trans. Terahertz Sci. Technol. 1 (1), 201-219 (2011).

J. Federici, "Review of moisture and liquid detection and mapping using terahertz imaging," J. Infrared Milli. Terahz. Waves 33 (2), 97-126 (2012).

E. Pickwell, B. E. Cole, A. J. Fitzgerald, V. P. Wallace and M. Pepper, "Simulation of terahertz pulse propagation in biological systems," Appl. Phys. Lett. 84 (12), 2190-2192 (2004).

E. Pickwell, B. E. Cole, A. J. Fitzgerald, M. Pepper and V. P. Wallace, "In vivo study of human skin using pulsed terahertz radiation," Phys. Med. Biol. 49 (9), 1595 (2004).

J. T. Kindt and C. A. Schmuttenmaer, "Far-infrared dielectric properties of polar liquids probed by femtosecond terahertz pulse spectroscopy," J. Phys. Chem. 100 (24), 10373-10379 (1996).

R. M. Woodward, V. P. Wallace, R. J. Pye, B. E. Cole, D. D. Arnone, E. H. Linfield and M. Pepper, "Terahertz Pulse Imaging of ex vivo Basal Cell Carcinoma," J. Investig. Dermatol. 120 (1), 72-78 (2003).

V. P. Wallace, A. J. Fitzgerald, S. Shankar, N. Flanagan, R. Pye, J. Cluff and D. D. Arnone, "Terahertz pulsed imaging of basal cell carcinoma ex vivo and in vivo," Br. J. Dermatol. 151 (2), 424-432 (2004).

R. M. Woodward, B. E. Cole, V. P. Wallace, R. J. Pye, D. D. Arnone, E. H. Linfield and M. Pepper, "Terahertz pulse imaging in reflection geometry of human skin cancer and skin tissue," Phys. Med. Biol. 47 (21), 3853 (2002).

A. J. Fitzgerald, V. P. Wallace, M. Jimenez-Linan, L. Bobrow, R. J. Pye, A. D. Purushotham and D. D. Arnone, "Terahertz pulsed imaging of human breast tumors," Radiology 239 (2), 533-540 (2006).

P. C. Ashworth, E. Pickwell-MacPherson, E. Provenzano, S. E. Pinder, A. D. Purushotham, M. Pepper and V. P. Wallace, "Terahertz pulsed spectroscopy of freshly excised human breast cancer," Opt. Express 17 (15), 12444-12454 (2009).

V. P. Wallace, A. J. Fitzgerald, E. Pickwell, R. J. Pye, P. F. Taday, N. Flanagan and T. Ha, "Terahertz Pulsed Spectroscopy of Human Basal Cell Carcinoma," Appl. Spectrosc. 60 (10), 1127-1133 (2006).

D. M. Mittleman, M. Gupta, R. Neelamani, R. G. Baraniuk, J. V. Rudd and M. Koch, "Recent advances in terahertz imaging," Appl. Phys. B 68 (6), 1085-1094 (1999).

Z. D. Taylor, R. S. Singh, M. O. Culjat, J. Y. Suen, W. S. Grundfest, H. Lee and E. R. Brown, "Reflective terahertz imaging of porcine skin burns," Opt. Lett. 33 (11), 1258-1260 (2008).

M. H. Arbab, T. C. Dickey, D. P. Winebrenner, A. Chen, M. B. Klein and P. D. Mourad, "Terahertz reflectometry of burn wounds in a rat model," Biomed. Opt. Express 2 (8), 2339-2347 (2011).

P. Tewari, C. Kealey, J. Sung, A. Maccabi, N. Bajwa, R. Singh, M. Culjat, A. Stojadinovic, W. Grundfest and Z. D. Taylor, "Advances in biomedical imaging using THz technology with applications to burn-wound assessment," Proc. SPIE 8261, 82610T (2012).

P. Tewari, C. P. Kealey, D. B. Bennett, N. Bajwa, K. S. Barnett, R. S. Singh, M. O. Culjat, A. Stojadinovic, W. S. Grundfest and Z. D. Taylor, "In vivo terahertz imaging of rat skin burns," J. Biomed. Opt. 17 (4), 040503 (2012).

M. H. Arbab, T. C. Dickey, D. P. Winebrenner, A. Chen and P. D. Mourad, "Characterization of burn injuries using terahertz time-domain spectroscopy," Proc. SPIE 7890, 78900Q (2011).

D. J. McGill, K. Sørensen, I. R. MacKay, I. Taggart and S. B. Watson, "Assessment of burn depth: A prospective, blinded comparison of laser Doppler imaging and videomicroscopy," Burns 33 (7), 833-842 (2007).

A. M. I. Watts, M. P. H. Tyler, M. E. Perry, A. H. N. Roberts and D. A. McGrouther, "Burn depth and its histological measurement," Burns 27 (2), 154-160 (2001).

\* cited by examiner

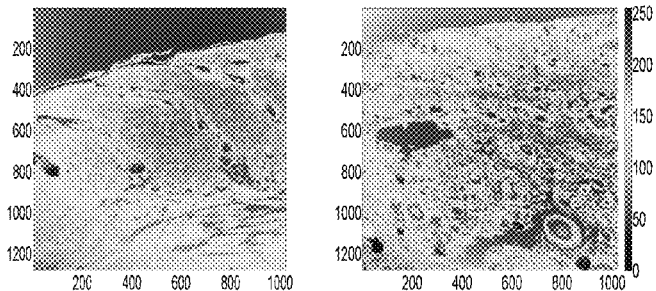
Fig 3(b)    Fig3(c)
Fig 4.
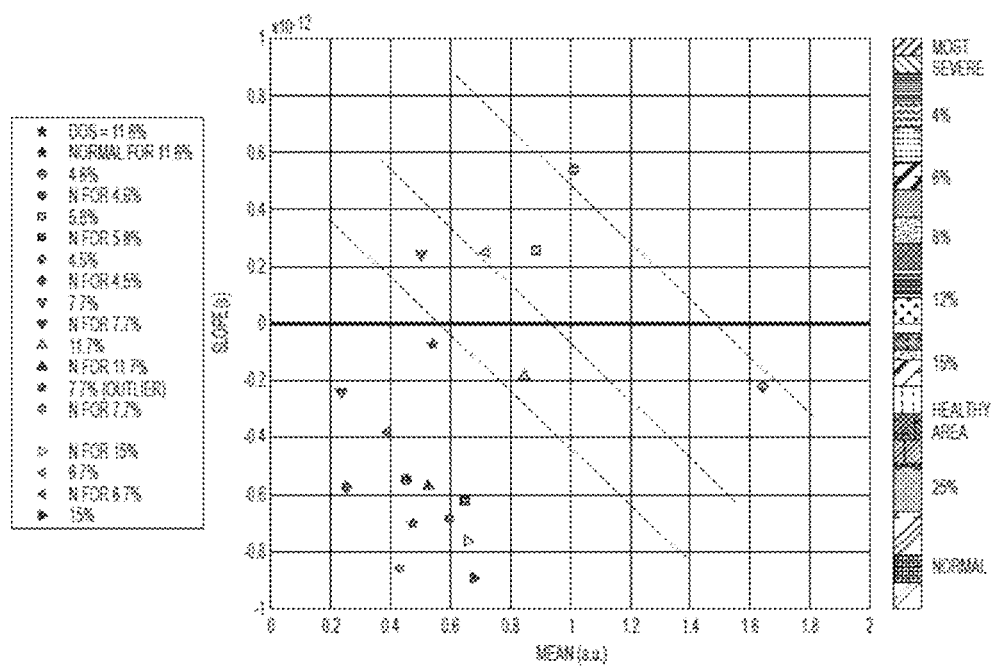

METHODS AND SYSTEMS FOR ASSESSING A BURN INJURY

CROSS REFERENCE

This application claims priority to U.S. Provisional Patent Application Ser. No. 61/587,179 filed Jan. 17, 2012, incorporated by reference herein in its entirety.

FEDERAL FUNDING STATEMENT

This invention was made with government support under N00014-09-1-0610, awarded by the Office of Naval Research (ONR). The government has certain rights in the invention.

COPYRIGHT NOTICE

Contained herein is material that is subject to copyright protection. The copyright owner reserves all rights to the copyright whatsoever.

BACKGROUND

With over one million burn injuries receiving medical treatment each year in the U.S., the social and economic costs, including recovery and reintegration burden, of burn survivors far exceed those of other injuries. Characterization of burn injuries during the early post-injury assessment period is a critical decision point in determining the management course, healing process, and ultimate outcome, since the treatment of a given burn differs considerably depending upon the results of the initial assessment. Burns are usually classified according to the depth of the damaged skin in three clinically useful categories: $1^{st}$, $2^{nd}$ and $3^{rd}$ degree burns. In a full-thickness or $3^{rd}$ degree burn, the entire depth of the skin, through the stratum corneum, epidermis and dermis layers, is destroyed. In a partial-thickness ($2^{nd}$ degree) burn the extent of the damage is contained within the dermis layer. Finally, $1^{st}$ degree or superficial burns only involve the epidermis layer of the skin, and usually heal without any scars or need for medical care. The clinical course of treatment is substantially different for burns of greater severity. Third degree injuries cannot heal without surgical and skin grafting procedures, whereas for $2^{nd}$ degree wounds, the recovery progress consists of careful monitoring and infection prevention over a 2-3 weeks period after the burn. During this period, a subgroup of the $2^{nd}$ degree burns will spontaneously heal, while others will develop to a full-thickness state and will require surgical intervention. The complex nature of partial-thickness burns is due to the extent of irreversible thermal damage to the microvasculature and the new epithelium generation sites. If an insufficient number of microvascular and epithelium generation structures survive after the injuries, the remaining viable parts of the dermis layer will slowly desiccate and eventually reach the $3^{rd}$ degree injury level.

The accuracy rate of current clinical assessment technique to differentiate between burn grades, based mainly on visual inspection by experienced surgeons, is only about 65-70%. Highly accurate differentiation and delineation of burn wounds can potentially alter management, reduce length of hospital stay and improve overall recovery for the burn patient. For instance, of value would be a noninvasive clinical diagnostic modality that could guide the treatment plan by predicting the healing outcome of $2^{nd}$ degree burns and guide surgical management to minimize scar formation.

SUMMARY OF THE INVENTION

In a first aspect, the present invention provides methods for assessing burn injuries, comprising (a) acquiring reflectivity measurements of burned tissue of a subject, wherein the reflectivity measurements are generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies; (b) determining a rate of change in the reflectivity measurements; and (c) determining a severity of the burn injury based on the rate of change.

In a second aspect, the present invention provides methods for self-calibration of a THz spectroscope, comprising (a) acquiring a sample-reference THz reflection signal from an air-sample reference slab interface; (b) for a sample reflectivity measurement taken using the THz spectroscope using the sample slab, acquiring a sample THz reflection signal from an air-sample slab interface, wherein the sample slab is the same thickness as the sample-reference slab; and (c) determining a corrected sample reflectivity measurement based on a difference between the sample THz reflection signal and the sample-reference THz reflection signal.

This method may further involve (d) acquiring a baseline-reference THz reflection signal from an air-baseline reference slab interface, wherein the baseline reference slab and the sample reference slab comprise the same material, wherein the baseline reference slab is at least twice as thick as the sample reference slab, and wherein the THz spectroscope includes a sample slab comprising the same material and having the same thickness as the sample reference slab; (e) determining a difference between the sample-reference THz reflection signal and the baseline-reference THz reflection signal to produce a differential THz reflection signal; (f) determining a difference between the corrected sample reflectivity measurement and the baseline-reference THz reflection signal to produce a baseline-removed corrected sample reflectivity measurement; (g) taking a Fourier transform of (i) the differential THz reflection signal and (ii) the baseline-removed corrected sample reflectivity measurement; and (h) determining a final corrected sample reflectivity measurement, wherein determining the final corrected sample reflectivity measurement comprises dividing the Fourier transform of the baseline-removed corrected sample reflectivity measurement by the Fourier transform of the differential THz reflection signal.

In a third aspect, the present invention provides computer-implemented methods, comprising (a) receiving reflectivity-measurement data indicating at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies; (b) determining a rate of change in the reflectivity measurements; (c) determining a severity of the burn injury based on the rate of change; and (d) causing an indication of the determined severity of the burn injury to be displayed on a graphical display.

In a fourth aspect, the present invention provides computing devices, comprising: at least one processor; a physical computer readable medium; and program instructions stored on the physical computer readable medium and executable by the at least one processor to cause the computing device to: (a) receive reflectivity-measurement data indicating at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies; (b) determine a rate of change in the reflectivity measurements; (c) determine a severity of the burn injury based on the rate of change; and (d) cause an indication of the determined severity of the burn injury to be displayed on a graphical display.

DESCRIPTION OF THE FIGURES

FIG. 4. The severity of burn injuries can be mapped out based on the mean and spectral slope of their THz reflectivity at 72 hour post-injury. The more severe burns (lower DOS values) are further apart from their normal control tissue (blue). The dashed lines=−x) are guide to the eye.

DETAILED DESCRIPTION OF THE INVENTION

Figure 1:
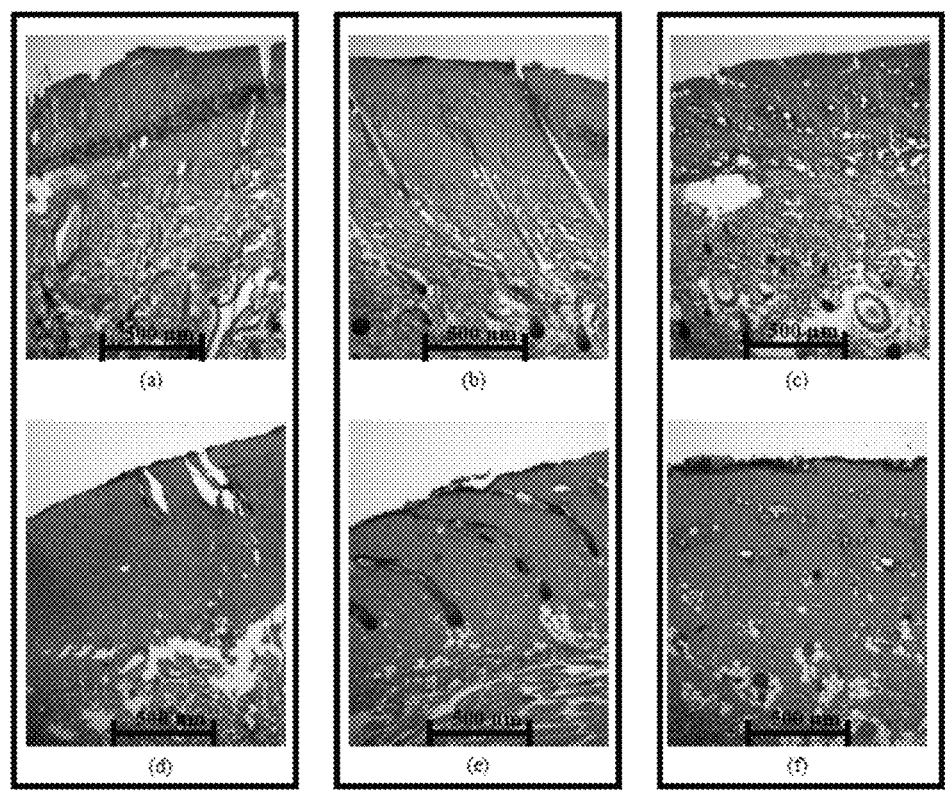
FIG. 1. H&E-stained microscope images from a representative group of the $2^{nd}$ (a-c) and $3^{rd}$ degree burns (d-f) obtained on day 3 post-injury. Three subgroups based on the nature and density of discrete structures within the skin layers were observed: (a) and (d) show a deep coagulation of the burned tissue with minor superficial skin cracks, (b) and (e) reveal existence of hair follicles in the burned regions of dermis, (c) and (f) show a large density of various discrete skin structures.

As used herein, the singular forms "a," "an" and "the" include plural referents unless the context clearly dictates otherwise. "And" as used herein is interchangeably used with "or" unless expressly stated otherwise.

All embodiments within and between different aspects of the invention can be combined unless the context clearly dictates otherwise.

As used herein "about" means+/−5% from the cited parameter.

As used herein the abbreviation "THz" refers to "Terahertz." In a first aspect, the present invention provides methods for assessing burn injuries, comprising (a) acquiring reflectivity measurements of burned tissue of a subject, wherein the reflectivity measurements are generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;

(b) determining a rate of change in the reflectivity measurements; and (c) determining a severity of the burn injury based on the rate of change.

As disclosed in detail herein, the inventors have shown that the methods of the invention allow for highly accurate differentiation and delineation of burn wounds, which can in turn more efficiently direct burn management, reduce length of hospital stay and improve overall recovery for the burn patient. The methods of the invention serve to eliminate guess work during multiple skin grafting operations, reduce scaring and reduce the length of patient hospitalization.

The subject can be any mammal, such as a human.

The radiation can be generated at the desired frequencies using any suitable means. Those of skill in the art are well aware of various techniques for generating radiation having frequencies within the recited range, including but not limited to backward wave oscillators, far infrared lasers, quantum cascade lasers, free electron lasers, photomixing sources, and non-linear optical (including but not limited to air plasma) sources, or photoconductive antenna sources commonly used in terahertz time domain spectrometers. The reflectivity measurements (i.e.: fraction of incident radiation that is reflected at the burn interface) can be acquired using any suitable means, dependent on the means for generating the radiation. Those of skill in the art are well aware of various means for acquiring reflectivity measurements generated by exposure of a substance to radiation having the frequencies used in the methods herein. In one embodiment, the radiation is applied at an angle of incidence between about 1° and about 60°; in various embodiments, the angle of incidence may be between about 1° and about 50, 1° and about 50°, 1° and about 45, 1° and about 30, 1° and about 20, 1° and about 10, 2° and about 10°, about 3° and about 10°, about 4° and about 10°, about 5° and about 10°, 1° or less than about 10°, 9°, 8°, 7°, 6°, 5°, 4°, 3°, or 2°.

In another embodiment, the radiation is generated by a terahertz spectrometer (for example; the use of THz time domain spectroscopy (THz-TDS)); such devices and their operation are known to those of skill in the art. Non-limiting and exemplary techniques for measuring reflectivity using terahertz time-domain spectroscopy are provided in the examples that follow. THz-TDS utilizes one or more pulses to generate the recited radiation at desired frequencies. In one embodiment, a single pulse can be used to generate the recited radiation at each of the plurality of frequencies. In another embodiment, the reflectivity measurement can be normalized via any suitable technique to limit the effect of drift of the THz-TDS device.

One exemplary and non-limiting suitable technique comprises:

(a) acquiring a sample-reference THz reflection signal from an air-sample reference slab interface;

(b) for a sample reflectivity measurement taken on the THz spectroscope using the sample slab, acquiring a sample THz reflection signal from an air-sample slab interface, wherein the sample slab is the same thickness as the sample-reference slab; and (c) determining a corrected sample reflectivity measurement based on a difference between the sample THz reflection signal and the sample-reference THz reflection signal. Such a technique may further involve:

(d) acquiring a baseline-reference THz reflection signal from an air-baseline reference slab interface, wherein the baseline reference slab and the sample reference slab comprise the same material, wherein the baseline reference slab is at least twice as thick as the sample reference slab, and wherein the THz spectroscope includes a sample slab comprising the same material and having the same thickness as the sample reference slab;

(e) determining a difference between the sample-reference THz reflection signal and the baseline-reference THz reflection signal to produce a differential THz reflection signal;

(f) determining a difference between the corrected sample reflectivity measurement and the baseline-reference THz reflection signal to produce a baseline-removed corrected sample reflectivity measurement;

(g) taking a Fourier transform of (i) the differential THz reflection signal and (ii) the baseline-removed corrected sample reflectivity measurement; and (h) determining a final corrected sample reflectivity measurement, wherein determining the final corrected sample reflectivity measurement comprises dividing the Fourier transform of the baseline-removed corrected sample reflectivity measurement by the Fourier transform of the differential THz reflection signal.

Another exemplary and non-limiting suitable technique comprises:

(a) acquiring a baseline-reference THz reflection signal from an air-baseline reference slab interface;

(b) acquiring a sample-reference THz reflection signal from an air-sample reference slab interface, wherein the baseline reference slab and the sample reference slab comprise the same material, wherein the baseline reference slab is at least twice as thick as the sample reference slab, and wherein the THz spectroscope includes a sample slab comprising the same material and having the same thickness as the sample reference slab;

(c) for a sample reflectivity measurement taken using the THz spectroscope using the sample slab, acquiring a sample THz reflection signal from an air-sample slab interface, wherein the sample slab is the same thickness as the sample-reference slab;

(d) determining a corrected sample reflectivity measurement based on a difference between the sample THz reflection signal and the sample-reference THz reflection signal;

(e) determining a difference between the sample-reference THz reflection signal and the baseline-reference THz reflection signal to produce a differential THz reflection signal;

(f) taking a Fourier transform of (i) the differential THz reflection signal and (ii) the corrected sample reflectivity measurement; and (g) determining a final corrected sample reflectivity measurement, wherein determining the final corrected sample reflectivity measurement comprises dividing the Fourier transform of the corrected sample reflectivity measurement by the Fourier transform of the differential THz reflection signal.

Figure 6:
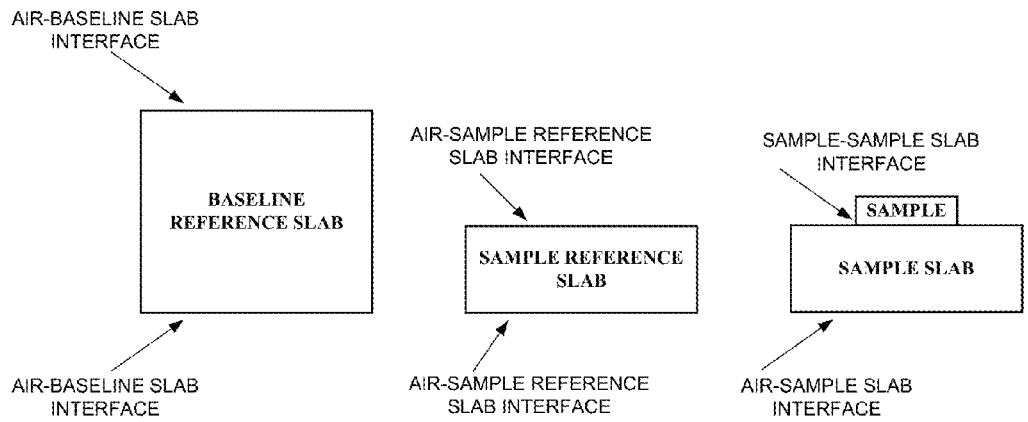
FIG. 6. Schematic presentation of air-slab and sample-slab interfaces.

A schematic illustration of air-slab and sample-slab interfaces is provided in FIG. 6. In a non-limiting embodiment, the method may comprise the following steps:

1. Acquire time-domain reflection signal from a 2*d (d may be some known thickness such as ¹⁄₁₆ inch) thick quartz (or some other known/fixed material with low terahertz attenuation) slab (i.e. Thick_ref).

2. Acquire time-domain reflection signal from 1*d thick quartz slab (i.e. Thin_ref).

3. Subtract Thick_ref from Thin_ref to get Differential_ref=Thin_ref−Thick_ref.

4. Take FFT (fourier transform) of Diff_ref for later "deconvolution" of subsequent sample measurements.

5. For each sample measurement, when sample is mounted on the 1*d thick quartz window (such as the 1*d thick quartz slab noted above), compare the reflection from the air/quartz interface with that of step 2, above. If there is any drift in the system power, determine a constant coefficient that may correct for such drift. This value may be referred to as Alpha.

6. Multiply the sample reflection signal from the quartz/sample interface by alpha to correct for the effect of the laser system power drift on the sample measurement.

7. Subtract Thick_ref from signal resulted from step 6.

8. Divide the FFT of the signal resulted from step 7, by that of step 4 (FFT of Diff_ref) to deconvolove the measurements and remove the system intrinsic response function. The resultant is the terahertz amplitude reflection spectrum of the sample, which is calibrated, baseline removed and deconvolved.

In another embodiment that can be combined with any other embodiment of the method disclosed herein, each reflectivity measurement comprises an average of several spatially disjointed reflectivity measurements for the respective frequency corresponding to that reflectivity measurement. This embodiment serves to control for inhomogeneity in the skin of the subject. As used herein, "spatially disjointed" means measurements at each frequency from 2 or more (i.e., 2, 3, 4, 5, 6, 7, 8, 9, 10, or more) positions at least one wavelength apart on the burned tissue. In this embodiment, these reflectivity measurements are then averaged for each frequency to provide the reflectivity measurement for that frequency.

Figure 2:
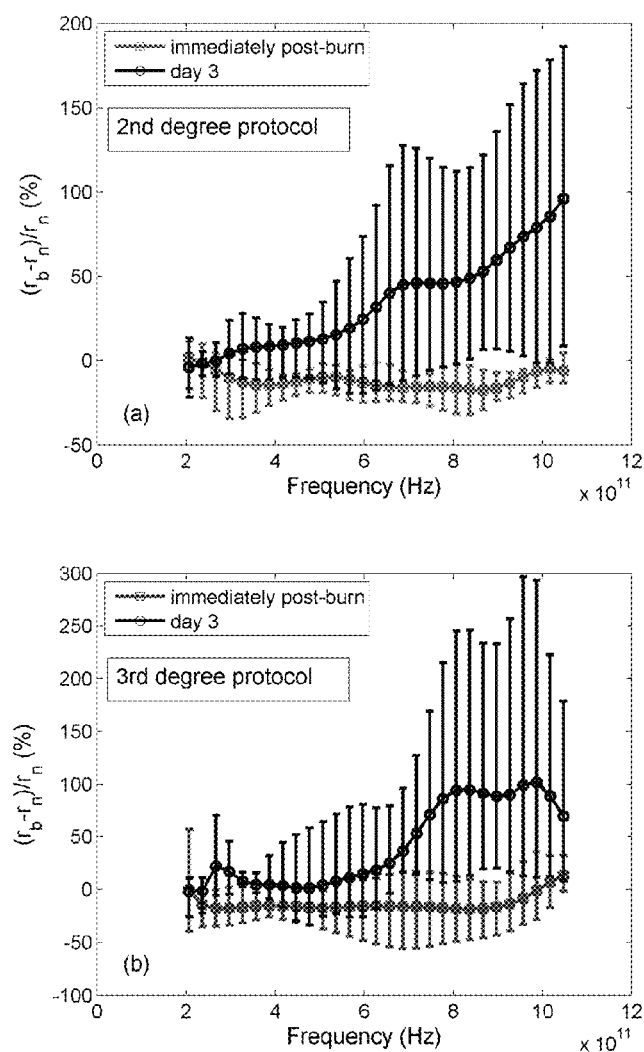
FIG. 2. (a) Normalized change in terahertz reflectivity of the $2^{nd}$ degree burns compared to normal skin (control experiment), measured immediately post-burn and on day 3, (b) same quantity for the $3^{rd}$ degree burns. The bars indicate full range of the experimental data obtained in our animal study.

As used herein, determining a "rate of change" in the reflectivity measurements includes any suitable way of measuring rates of change in the reflectivity measurements. In one embodiment, the rate of change comprises or consists of a "rate of change" in reflectivity measurements between different frequencies (i.e. spectral slope) in the plurality of radiation frequencies at a single time point; this embodiment provides a "fingerprint" of reflectivity at multiple frequencies at a single time point. In another embodiment, the "rate of change" comprises or consists of a rate of change in reflectivity measurements at individual frequencies over time. For instance, a rate of change for excess reflectivity compared to healthy tissue in percentage can be calculated by, $$\frac{r_b - r_n}{r_n} \times 100, \tag{1}$$

where $r_b$ and $r_n$ are the Fourier transformed reflection amplitudes of the burned and normal skin, respectively, which are resultants of the step 8 in signal processing steps above. Experimental results based on rate of change calculations according to Equation (1) are shown in FIG. 2(*a*) and (*b*).

Based on the teachings herein, it is within the level of skill in the art to determine other ways to measure the rate of change of the reflectivity measurements.

In various further embodiments, the radiation frequencies comprise or consist of frequencies at least between about 0.01 THz and about 30 THz; about 0.1 THz and about 30 THz; about 0.001 THz and about 20 THz; about 0.001 THz and about 10 THz; about 0.001 THz and about 5 THz; about 0.001 THz and about 3 THz; about 0.001 THz and about 2 THz; about 0.001 THz and about 1.5 THz; about 0.001 THz and about 1.1 THz; about 0.01 THz and about 20 THz; about 0.01 THz and about 10 THz; about 0.01 THz and about 5 THz; about 0.01 THz and about 3 THz; about 0.01 THz and about 2 THz; about 0.01 THz and about 1.5 THz; about 0.01 THz and about 1.1 THz; about 0.1 THz and about 20 THz; about 0.1 THz and about 10 THz; about 0.1 THz and about 5 THz; about 0.1 THz and about 3 THz; about 0.1 THz and about 2 THz; about 0.1 THz and about 1.5 THz; and about 0.1 THz and about 1.1 THz.

As used herein, a "plurality" of frequencies means at least 2 radiation frequencies. In various further embodiments, the plurality of frequencies comprises at least 3, 4, 5, 6, 7, 8, 9, 10, 15, 20, 25, 50, 75, 100, 150, 200, 250, 300, 350, 400, 450, 500, or more different radiation frequencies between about 0.001 THz and about 30 THz.

In one embodiment, each reflectivity measurements can optionally be further processed prior to determining the rate of change. In one embodiment, the reflectivity measurement is processed to limit (i.e.: reduce by any suitable amount, such as by 25%, 50%, 75%, 90%, 95%, or 100%) the effect of baseline waveform interference. For instance, a reflectivity measurement from an air interface of a reference slab may be subtracted from the reflectivity measurement. Removal of this portion of the signal provides for removal of baseline interference due to the air interface of the sample slab.

Moreover, processing of the signal can comprise any conditioning of the reflectivity measurement via suitable signal processing techniques, including but not limited to those described herein. Similarly, any suitable signal processing steps can be included to improve reflectivity measurement quality (i.e.: noise reduction, signal enhancement, echo cancelation, etc.), to compress reflectivity measurement signals, to extract reflectivity measurement features, etc. For instance, processing the reflectivity measurement may involve dividing a Fourier transform of a sample reflectivity measurement by a Fourier transform of a differential THz reflection signal, as noted above. In such a case, the differential THz reflection signal may be determined based on a difference between a sample-reference THz reflection signal acquired from an air-sample reference slab interface and a baseline-reference THz reflection signal baseline-reference THz reflection signal acquired from an air-baseline reference slab interface.

In another non-limiting embodiment, each reflectivity measurement is corrected to account for drift. For instance, processing the reflectivity measurement may involve acquiring a THz reference reflection signal from a reference slab interface (such as the sample-reference THz reflection signal acquired from the air-sample reference slab interface discussed above). Then, the process may involve, for a sample reflectivity measurement taken on the THz spectroscope using the sample slab, acquiring a sample THz reflection signal from an air-sample slab interface of the sample slab (as discussed above). Then the process may involve determining a corrected sample reflectivity measurement based on a difference between the sample THz reflection signal and the sample-reference THz reflection signal.

Determining the corrected sample reflectivity measurement based on the difference between the sample THz reflection signal and the sample-reference THz reflection signal may involve determining that the difference between the sample THz reflection signal and the sample-reference THz reflection signal indicates a drift in a power of the THz spectroscope. Further, determining the corrected sample reflectivity measurement may involve multiplying the sample reflectivity measurement by a factor that corrects for the drift in the power of the THz spectroscope. Then, as noted above, a reflectivity measurement from an air interface of a baseline reference slab, thicker than the sample slab, may be subtracted from the reflectivity measurement. Removal of this portion of the signal provides for removal of baseline interference due to the air interface reflection of the sample slab.

As used herein, the "one or more appropriate times post-burn" can be any time after the subject sustains the burn and prior to burn healing, and when the severity of the burn or the most appropriate course of treatment have not been determined. As will be understood by those of skill in the art, the "appropriate" time post-burn will vary from subject to subject depending on a variety of factors. In general, the one or more appropriate times post-burn are between immediately after burn injury to about 14 days post-burn. In various embodiments, the one or more appropriate times post-burn are between immediately after burn injury to about 13 days post-burn, immediately after burn injury to about 12 days post-burn, immediately after burn injury to about 11 days post-burn, immediately after burn injury to about 10 days post-burn, immediately after burn injury to about 9 days post-burn, immediately after burn injury to about 8 days post-burn, immediately after burn injury to about 7 days post-burn, immediately after burn injury to about 6 days post-burn, immediately after burn injury to about 5 days post-burn, immediately after burn injury to about 4 days post-burn, immediately after burn injury to about 3 days post-burn, about 12 hours after burn injury to about 13 days post-burn, about 12 hours after burn injury to about 12 days post-burn, about 12 hours after burn injury to about 11 days post-burn, about 12 hours after burn injury to about 10 days post-burn, about 12 hours after burn injury to about 9 days post-burn, about 12 hours after burn injury to about 8 days post-burn, about 12 hours after burn injury to about 7 days post-burn, about 12 hours after burn injury to about 6 days post-burn, about 12 hours after burn injury to about 5 days post-burn, about 12 hours after burn injury to about 4 days post-burn, about 12 hours after burn injury to about 3 days post-burn, about 24 hours after burn injury to about 13 days post-burn, about 24 hours after burn injury to about 12 days post-burn, about 24 hours after burn injury to about 11 days post-burn, about 24 hours after burn injury to about 10 days post-burn, about 24 hours after burn injury to about 9 days post-burn, about 24 hours after burn injury to about 8 days post-burn, about 24 hours after burn injury to about 7 days post-burn, about 24 hours after burn injury to about 6 days post-burn, about 24 hours after burn injury to about 5 days post-burn, about 24 hours after burn injury to about 4 days post-burn, about 24 hours after burn injury to about 3 days post-burn, and between about 1 hour-72 hours, 2 hours-72 hours, 3 hours-72 hours, 4 hours-72 hours, 5 hours-72 hours, 6 hours-72 hours, 7 hours-72 hours, 8 hours-72 hours, 9 hours-72 hours, 10 hours-72 hours, 12 hours-72 hours, 14 hours-72 hours, 16 hours-72 hours, 18 hours-72 hours, 20 hours-72 hours, 22 hours-72 hours, 24 hours-72 hours; 30 hours-72 hours, 36 hours-72 hours, 42-hours-72 hours, or 48 hours-72 hours post-burn.

In certain embodiments, such as when measuring a rate of change of reflectivity between different radiation frequencies, the subject can be exposed to the plurality of radiation frequencies one time. In certain other embodiments, such as when measuring a rate of change of reflectivity over time at a given radiation frequency, the subject can be exposed to the plurality of radiation frequencies two or more (i.e., 2, 3, 4, 5, or more) times.

The methods of the invention are used to determine severity of the burn injury based on the rate of change of the reflectivity measurements. The inventors have shown that the rates of change of reflectivity measurements obtained using the methods of the invention can be used to non-invasively determine severity of the burn injury. The methods are able to distinguish between full thickness burns (which require surgical intervention for healing) and partial thickness burns (which may heal without surgical intervention). Thus, the methods provide a non-invasive means for rapidly identifying those subjects that are likely to require surgical intervention, and those that may not require surgical intervention. The methods are also able to distinguish between superficial partial thickness wounds (which will likely heal spontaneously) and deep partial thickness wounds (which may not heal spontaneously). The methods thus further provide a means to identify those patients with partial thickness burns that will likely require surgical intervention, and those whose wounds are more likely to heal naturally. Furthermore, the methods provide an accurate means to delineate margins of full-thickness burns from the partial-thickness burns that can heal spontaneously during skin grafting surgical procedures.

Determining severity of the burn injury based on the rate of change may comprise the use of any suitable calculations or analyses to further refine the subject stratification. In one embodiment, the rate of change is compared to a suitable control, including but not limited to rates of change previously determined from patient populations with full thickness burns, partial thickness burns, and/or non-burned skin. In another embodiment, the control is the rate of change as compared to unburned skin from the subject that the method is being carried out on. In another non-limiting embodiment, determining severity of the burn comprises calculating a correlation between the THz reflectivity and the rate of change. In one non-limiting embodiment, the correlation comprises a linear correlation that may take any suitable form, including but not limited to equation $Z=(a \cdot R)+(b \cdot S)$ or $Z=(a \cdot R)-(b \cdot S)$, wherein Z is a measure of burn severity, "R" is the THz reflectivity, "S" is the rate of change, and "a" and "b" are arbitrary coefficients, wherein $0<a$ and $b \leq 1$. In another embodiment, the correlation may be any suitable ratio of R and S, including but not limited to $Z=(a \cdot R)/(b \cdot S)$ or $Z=(b \cdot S)/(a \cdot R)$, wherein $0<a$ and $b \leq 1$. It will be understood by those of skill in the art based on the teachings herein that many such variations on suitable calculations can be used with the methods of the present invention.

In a further embodiment, the method further comprises treating the burn injury based on the determined severity of the burn injury. Current clinical approaches at burn centers consist of patient stabilization, replenishing of vital liquids, cleaning and infection prevention within the first 24 hours to 72 hours while managing pain and diagnosing the areas where skin grafting is necessary. Obtaining skin grafts (often from the patient directly) and beginning surgical intervention and repair is a repetitive process that occurs over and over again during the next several weeks. Thus, for example, those subjects identified by the methods of the invention as having full thickness burns or deep partial thickness burns, can be more rapidly treated by skin grafting or other appropriate treatment as determined by an attending physician based on all circumstances. In another non-limiting embodiment, a subject identified as having a superficial partial thickness burn can receive appropriate treatment other than skin grafting as determined by an attending physician based on all circumstances.

In a second aspect, the present invention provides methods for self-calibration of a THz spectroscope. These methods can be used for any use of a THz spectroscope, including but not limited to those uses disclosed in the first aspect of the invention. In one embodiment, the methods comprise:

(a) acquiring a sample-reference THz reflection signal from an air-sample reference slab interface;

(b) for a sample reflectivity measurement taken on the THz spectroscope using the sample slab, acquiring a sample THz reflection signal from an air-sample slab interface, wherein the sample slab has the same thickness as the sample-reference slab; and (c) determining a corrected sample reflectivity measurement based on a difference between the sample THz reflection signal and the sample-reference THz reflection signal.

The method may further comprise:

(d) acquiring a baseline-reference THz reflection signal from an air-baseline reference slab interface, wherein the baseline reference slab and the sample reference slab comprise the same material, wherein the baseline reference slab is at least twice as thick as the sample reference slab, and wherein the THz spectroscope includes a sample slab comprising the same material and having the same thickness as the sample reference slab;

(e) determining a difference between the sample-reference THz reflection signal and the baseline-reference THz reflection signal to produce a differential THz reflection signal;

(f) determining a difference between the corrected sample reflectivity measurement and the baseline-reference THz reflection signal to produce a baseline-removed corrected sample reflectivity measurement;

(g) taking a Fourier transform of (i) the differential THz reflection signal and (ii) the baseline-removed corrected sample reflectivity measurement; and (h) determining a final corrected sample reflectivity measurement, wherein determining the final corrected sample reflectivity measurement comprises dividing the Fourier transform of the baseline-removed corrected sample reflectivity measurement by the Fourier transform of the differential THz reflection signal.

In another embodiment, the methods comprise:

(a) acquiring a baseline-reference THz reflection signal from an air-baseline reference slab interface;

(b) acquiring a sample-reference THz reflection signal from an air-sample reference slab interface, wherein the baseline reference slab and the sample reference slab comprise the same material, wherein the baseline reference slab is at least twice as thick as the sample reference slab, and wherein the THz spectroscope includes a sample slab comprising the same material and having the same thickness as the sample reference slab;

(c) for a sample reflectivity measurement taken on the THz spectroscope using the sample slab, acquiring a sample THz reflection signal from an air-sample slab interface, wherein the sample slab is the same thickness as the sample-reference slab;

(d) determining a corrected sample reflectivity measurement based on a difference between the sample THz reflection signal and the sample-reference THz reflection signal;

(e) determining a difference between the sample-reference THz reflection signal and the baseline-reference THz reflection signal to produce a differential THz reflection signal;

(f) taking a Fourier transform of (i) the differential THz reflection signal and (ii) the corrected sample reflectivity measurement; and (g) determining a final corrected sample reflectivity measurement, wherein determining the final corrected sample reflectivity measurement comprises dividing the Fourier transform of the corrected sample reflectivity measurement by the Fourier transform of the differential THz reflection signal.

Determining the corrected sample reflectivity measurement based on the difference between the sample THz reflection signal and the sample-reference THz reflection signal may involve determining that the difference between the sample THz reflection signal and the sample-reference THz reflection signal indicates a drift in a power of the THz spectroscope. Further, determining the corrected sample reflectivity measurement may involve multiplying the sample reflectivity measurement by a factor that corrects for the drift in the power of the THz spectroscope. Then, the correction may involve subtracting from the corrected sample reflectivity measurement the baseline-reference THz reflection signal. Removal of the baseline-reference THz reflection signal provides for removal of baseline interference due to the air interface reflection of the sample slab.

Note that, in an embodiment, the sample slab and the sample-reference slab may be the same slab.

Further, references to the "air" component of any "air-slab interface" described herein should be understood to include any suitable medium such as ambient air, or some other inert gas, such as N2, Argon, or other suitable gas, or a fiber medium.

A schematic illustration of air-slab and slab-sample interfaces is provided in FIG. 6.

In a non-limiting embodiment, the method may comprise the following steps:

1. Acquire time-domain reflection signal from a 2*d (d may be some known thickness such as $\frac{1}{16}$ inch) thick quartz (or some other known/fixed material with low terahertz attenuation) slab (i.e. Thick_ref).

2. Acquire time-domain reflection signal from 1*d thick quartz slab (i.e. Thin_ref).

3. Subtract Thick_ref from Thin_ref to get Differential_ref=Thin_ref−Thick_ref.

4. Take FFT (fourier transform) of Diff_ref for later "deconvolution" of subsequent sample measurements.

5. For each sample measurement, when sample is mounted on the 1*d thick quartz window (such as the 1*d thick quartz slab noted above), compare the reflection from the air/quartz interface with that of step 2, above. If there is any drift in the system power, correct for that amplitude change by multiplying the measured signal by a constant coefficient to numerically restore the reflected signal amplitude from air/quartz interface. In other words, determine a constant coefficient that may correct for any drift in the system power over time. This value may be referred to as Alpha.

6. Multiply the second reflection signal from the quartz/sample interface by alpha to correct for the effect of the laser system power drift on the sample measurement.

7. Subtract Thick_ref from signal resulted from step 6.

8. Divide the FFT of the signal resulted from step 7, by that of step 4 (FFT of Diff_ref) to deconvolove the measurements and remove the system intrinsic response function. The resultant is the terahertz amplitude reflection spectrum of the sample, which is both calibrated and deconvolved.

In a third aspect, the present invention provides computer-implemented methods, comprising:

(a) receiving reflectivity-measurement data indicating at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;

(b) determining a rate of change in the reflectivity measurements;

(c) determining a severity of the burn injury based on the rate of change; and (d) causing an indication of the determined severity of the burn injury to be displayed on a graphical display.

The computer-implemented methods may comprise any embodiment or combination of embodiments disclosed for the methods of the first and/or second aspect of the invention. For example, in one embodiment, the computer-implemented method may further comprise, before receiving the reflectivity-measurement data, causing the at least one reflectivity measurement to be performed using THz time domain spectroscopy (THz-TDS). In another embodiment, the computer-implemented method may further comprise, before determining the rate of change, normalizing the at least one reflectivity measurement to limit effect of drift of a device used to generate the radiation. Other embodiments and combinations of embodiments will be readily apparent to those of skill in the art based on the teachings herein.

The computer-implemented method may be carried out by any suitable computing system and/or computing device such as example computing device 700 discussed further below with respect to FIG. 7.

In a fourth aspect, the present invention provides computing devices, comprising:

at least one processor;

a physical computer readable medium; and program instructions stored on the physical computer readable medium and executable by the at least one processor to cause the computing device to:

(a) receive reflectivity-measurement data indicating at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;

(b) determine a rate of change in the reflectivity measurements;

(c) determine a severity of the burn injury based on the rate of change; and (d) cause an indication of the determined severity of the burn injury to be displayed on a graphical display.

The computing devices may comprise any embodiment or combination of embodiments disclosed for the methods of the invention. For example, in one embodiment, the computing device may further comprise program instructions stored on the physical computer readable medium and executable by the at least one processor to cause the computing device to: before receiving the reflectivity-measurement data, cause the at least one reflectivity measurement to be performed using THz time domain spectroscopy (THz-TDS). In another embodiment, the computing device may further comprise program instructions stored on the physical computer readable medium and executable by the at least one processor to cause the computing device to, before determining the rate of change, normalize the at least one reflectivity measurement to limit effect of drift of a device used to generate the radiation. Other embodiments and combinations of embodiments will be readily apparent to those of skill in the art based on the teachings herein.

Figure 7:
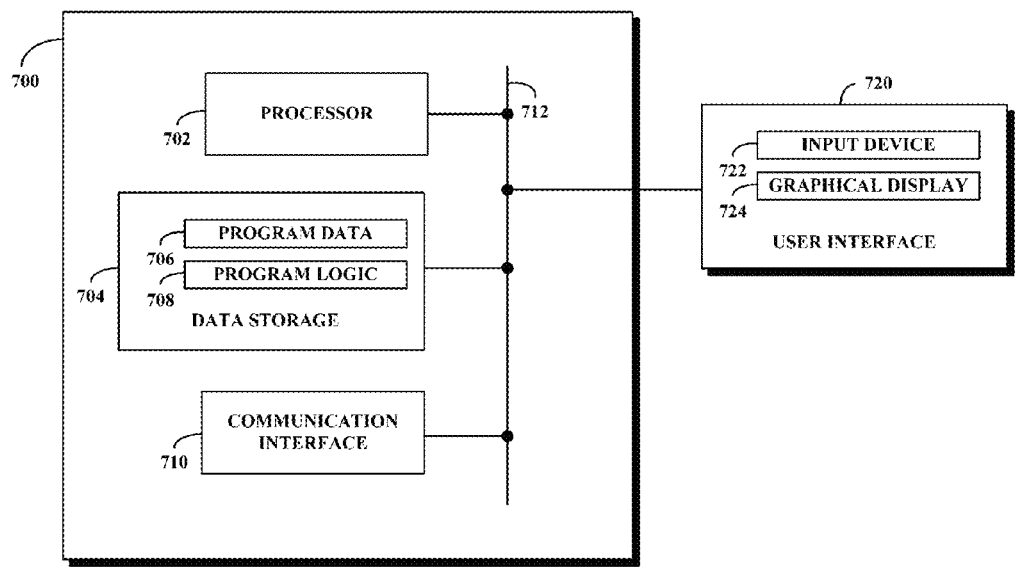
FIG. 7. Simplified block diagram of an example computing system arranged to implement aspects of the methods described herein.

FIG. 7 includes a simplified block diagram of an example computing system that may be arranged to implement aspects of the methods described herein. Example computing device 700 as shown in FIG. 7 may include processor 702, data storage 704, and communication interface 710, all linked together via system bus, network, or other connection mechanism 712.

Processor 702 may include one or more general purpose microprocessors and/or one or more dedicated signal processors and may be integrated in whole or in part with communication interface 710. Data storage 704 may include memory and/or other storage components, such as optical, magnetic, organic or other memory disc storage, which can be volatile and/or non-volatile, internal and/or external, and integrated in whole or in part with processor 702. Data storage 704 may be arranged to contain (i) program data 706 and (ii) program logic 708. Although these components are described herein as separate data storage elements, the elements could just as well be physically integrated together or distributed in various other ways. For example, program data 706 may be maintained in data storage 704 separate from program logic 708, for easy updating and reference by program logic 708.

Communication interface 710 typically functions to communicatively couple computing device 700 to networks, such as a public network. As such, communication interface 710 may include a wired (e.g., Ethernet) and/or wireless (e.g., Wi-Fi) packet-data interface, for communicating with other devices, entities, and/or networks. Computing device 700 may also include multiple interfaces 710, such as one through which computing device 700 sends communication, and one through which computing device 700 receives communication.

Computing device 700 may also include, or may be otherwise communicatively coupled to, user interface 720. User interface 720 may include input device 722 including, for example, buttons, a touch screen, a microphone, and/or any other elements for receiving inputs. User interface 720 may also include one or more elements for communicating outputs, for example, one or more graphical displays 724 and/or a speaker. In operation, user interface 720 may be configured to display a graphical user interface (GUI) via graphical display 724 and may also be configured to receive inputs, via input device 722, corresponding to use of such a GUI.

It should be understood that the arrangement of example computing device 700 set forth in FIG. 7 and other arrangements described herein are set forth only as examples. Those skilled in the art will appreciate that other arrangements and elements (e.g., machines, interfaces, functions, orders, and groupings of functions, etc.) can be used instead and that some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. And various functions described herein may be carried out by a processor executing instructions stored in memory.

In a fifth aspect, the present invention provides physical computer-readable media having computer executable instructions stored thereon, the instructions comprising:

(a) instructions for receiving reflectivity-measurement data indicating at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;

(b) instructions for determining a rate of change in the reflectivity measurements;

(c) instructions for determining a severity of the burn injury based on the rate of change; and (d) instructions for causing an indication of the determined severity of the burn injury to be displayed on a graphical display.

The physical computer-readable media may comprise any embodiment or combination of embodiments disclosed for the methods of the invention. For example, in one embodiment, the instructions may further comprise instructions for, before receiving the reflectivity-measurement data, causing the at least one reflectivity measurement to be performed using THz time domain spectroscopy (THz-TDS). In another embodiment, the instructions may further comprise instructions for, before determining the rate of change, normalizing the at least one reflectivity measurement to limit effect of drift of a device used to generate the radiation. Other embodiments and combinations of embodiments will be readily apparent to those of skill in the art based on the teachings herein.

Figure 8:
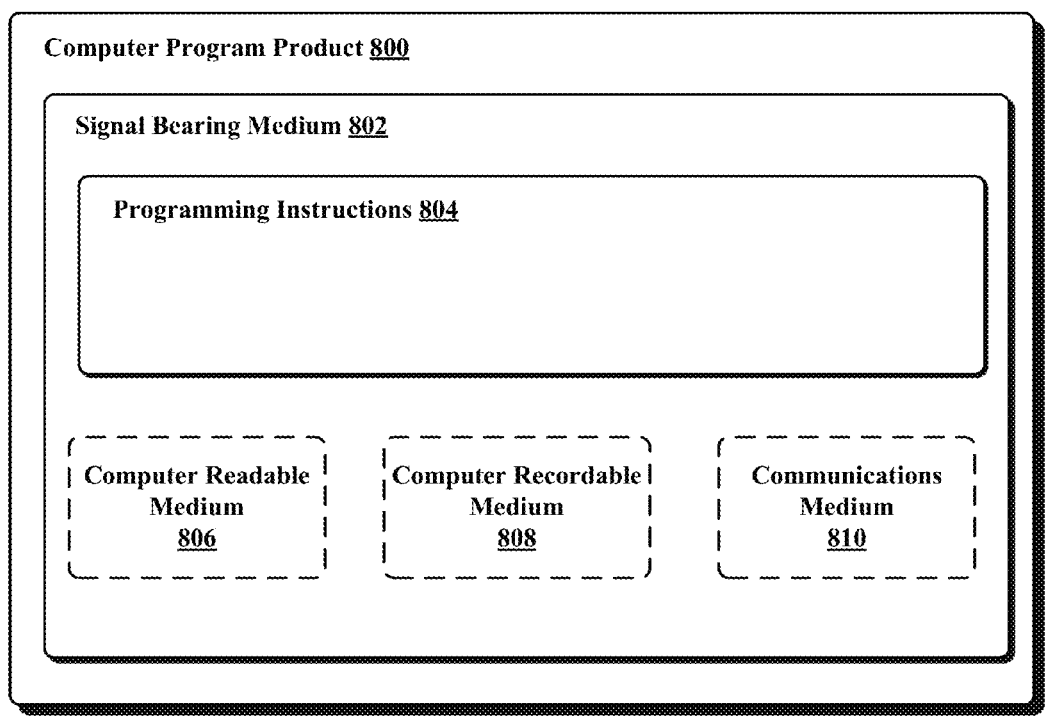
FIG. 8. Simplified schematic of an example computer-readable medium arranged to implement aspects of the methods described herein.

The instructions may be encoded on a physical, and/or non-transitory, computer readable storage media in a machine-readable format, or on other non-transitory media or articles of manufacture. FIG. 8 is a schematic illustrating a conceptual partial view of an example computer program product that includes a computer program for executing a computer process on a computing device, arranged according to at least some embodiments presented herein.

In one embodiment, the example computer program product 800 is provided using a signal bearing medium 802. The signal bearing medium 802 may include one or more programming instructions 804 that, when executed by one or more processors may provide functionality or portions of the functionality described herein. In some examples, the signal bearing medium 802 may encompass a computer-readable medium 806, such as, but not limited to, a hard disk drive, a Compact Disc (CD), a Digital Video Disk (DVD), a digital tape, memory, etc. In some implementations, the signal bearing medium 802 may encompass a computer recordable medium 808, such as, but not limited to, memory, read/write (R/W) CDs, R/W DVDs, etc. In some implementations, the signal bearing medium 802 may encompass a communications medium 810, such as, but not limited to, a digital and/or an analog communication medium (e.g., a fiber optic cable, a waveguide, a wired communications link, a wireless communication link, etc.). Thus, for example, the signal bearing medium 802 may be conveyed by a wireless form of the communications medium 810. It should be understood, however, that computer-readable medium 806, computer recordable medium 808, and communications medium 810 as contemplated herein are distinct mediums and that, in any event, computer-readable medium 808 is a physical, non transitory, computer-readable medium.

The one or more programming instructions 804 may be, for example, computer executable and/or logic implemented instructions. In some examples, a computing device such as the computing device 700 of FIG. 7 may be configured to provide various operations, functions, or actions in response to the programming instructions 804 conveyed to the computing device 700 by one or more of the computer readable medium 806, the computer recordable medium 808, and/or the communications medium 810.

The non-transitory computer readable medium could also be distributed among multiple data storage elements, which could be remotely located from each other. The computing device that executes some or all of the stored instructions could be a computing device such as the computing device 700 illustrated in FIG. 7.

EXAMPLES

A diagnosis criterion is proposed for non-invasive grading of burn injuries using terahertz radiation. Experimental results are presented from in vivo terahertz time-domain spectroscopy of $2^{nd}$ and $3^{rd}$ degree wounds, obtained in a 72-hours animal study. During this period, the change in the spectroscopic response of the burned tissue is studied. It is shown that terahertz waves are sensitive to not only the post burn formation of interstitial edema, but also to the density of skin structures. Based on these results, it is proposed that the combination of these two effects, as probed by terahertz spectroscopy of the tissue, may be used to differentiate partial-thickness burns that will naturally heal from those that will require surgical intervention.

With over one million burn injuries receiving medical treatment each year in the U.S., the social and economic costs, including recovery and reintegration burden, of burn survivors far exceed those of other injuries[1-2]. Characterization of burn injuries during the early post-injury assessment period is a critical decision point in determining the management course, healing process, and ultimate outcome, since the treatment of a given burn differs considerably depending upon the results of the initial assessment. Burns are usually classified according to the depth of the damaged skin in three clinically useful categories: $1^{st}$, $2^{nd}$ and $3^{rd}$ degree burns [2]. In a full-thickness or $3^{rd}$ degree burn, the entire depth of the skin, through the stratum corneum, epidermis and dermis layers, is destroyed. In a partial-thickness ($2^{nd}$ degree) burn the extent of the damage is contained within the dermis layer. Finally, $1^{st}$ degree or superficial burns only involve the epidermis layer of the skin, and usually heal without any scars or need for medical care. The clinical course of treatment is substantially different for burns of greater severity. Third degree injuries cannot heal without surgical and skin grafting procedures, whereas for $2^{nd}$ degree wounds, the recovery progress consists of careful monitoring and infection prevention over a 2-3 weeks period after the burn[2-3]. During this period, a subgroup of the $2^{nd}$ degree burns will spontaneously heal, while others will develop to a full-thickness state and will require surgical intervention. The complex nature of partial-thickness burns is due to the extent of irreversible thermal damage to the microvasculature and the new epithelium generation sites. If an insufficient number of microvascular and epithelium generation structures survive after the injuries, the remaining viable parts of the dermis layer will slowly desiccate and eventually reach the $3^{rd}$ degree injury level[2,4]. Therefore, in order to investigate the utility of a diagnosis technique for differentiating $2^{nd}$ degree burns from $3^{rd}$ degree ones, in vivo animal models should be employed, as opposed to ex vivo studies, due to the complex dynamics of wound healing after thermal injury.

The accuracy rate of current clinical assessment technique to differentiate between burn grades, based mainly on visual inspection by experienced surgeons, is only about 65-70%[2,5] Highly accurate differentiation and delineation of burn wounds can potentially alter management, reduce length of hospital stay and improve overall recovery for the bun patient. Attempts at developing such diagnostic tools have been made, but have not resulted in tools able to achieve sufficient specificity and sensitivity, as compared to histological assessment of wound biopsies. Moreover, significant issues have limited the implementation of any such modalities in clinical environments, such as cost effectiveness and compatibility to routine patient care.

The terahertz part of the electromagnetic spectrum, known as the so-called "THz gap," is usually defined by the frequencies between 100 GHz and 10 THz (wavelengths from 3 mm to 30 μm)[14]. The high absorption of terahertz radiation by both bound and free water molecules provides a sensitive signal contrast for imaging applications[15]. Difference in the water content of the tissue has been recently proposed as the main basis for many biomedical and biological applications of terahertz radiation[16-18]. Pickwell et al. furthermore showed that a double Debye dielectric relaxation model can be used to describe the terahertz response of healthy human skin[19-20], which is very similar to the model often used for polar liquids[21]. Pulsed terahertz emissions have also been used to image and delineate Basal Cell Carcinoma (BCC)[22-24], and human breast cancer tumor margms[25-26], based on the difference in the water content of the cancerous tumor versus healthy tissue[27].

In this example, we formulate a hypothesis for a burn diagnosis criterion based on the in vivo terahertz reflection spectroscopy results obtained from $2^{nd}$ and $3^{rd}$ degree burns over a 72-hours period after injury. In order to do so, we first introduce an image processing approach to objectively quantify the density of skin structures (DOS). We then show that a strong statistical correlation exists between the THz observations and the DOS metric.

The experimental animal model and burn protocol used in this study was approved by the Institutional Animal Care and Use Committee at the University of Washington. Male Sprague-Dawley rats (n=9), weighing between 300 g and 400 g, were divided into two groups. After the animal was anesthetized with isoflurane (4% for induction, 2% for maintenance, with $O_2$ flow rate of 1 liter/minute), its back was shaved and epilated with hair remover lotion (Nair, Church & Dwight Co, Princeton, N.J.). Two posterior sites corresponding to approximately the $12^{th}$ thoracic vertebra were marked 3 cm laterally off from the midline on either sides of the rats, one to create a burn and the other as the control tissue. Each group of rats received either a $2^{nd}$ degree (n=5), 100° C. for 3 seconds, or $3^{rd}$ degree (n=4), 100° C. for 30 seconds, burn while being maintained under analgesics for the duration of the experiments. A 313 g brass rod, with a 1 cm diameter cylindrical protrusion, was heated in a water bath maintained at 100° C. The cylindrical protrusion was then held against the marked site for the specified time using only the weight of the rod. Terahertz time domain spectroscopy (THz-TDS) was used to measure the reflectivity of both control and burned tissue at a near normal incidence angle)(θ~10° immediately and 72 hours post-burn. After the conclusion of the terahertz experiments on the $3^{rd}$ day, and after euthanasia by an overdose of pentobarbital (250 mg/kg), biopsy samples were collected using a 3 mm biopsy punch. H&E-stained histology of all samples confirmed the consistent formation of $2^{nd}$ degree and the $3^{rd}$ degree burns using this protocol.

THz-TDS technique: The Terahertz Time-Domain Spectroscopy (THz-TDS) setup used in this study consisted of an 800 nm, 50 fs Ti:Saphire laser, which by impinging upon a biased photoconductive antenna, built with 100 μm gap on low-temperature GaAs, generated the Terahertz waves. Terahertz radiation was first collimated and then focused, using a pair of off-axis parabolic gold mirrors, on the samples placed on a fused silica imaging window (sample slab). Upon reflection from the burned and normal skin samples, the terahertz waves were detected via the electro-optic sampling method in a ZnTe crystal. The entire THz-TDS system was enclosed in a box and purged with dry $N_2$ to eliminate the absorption features of ambient humidity from the experimental results.

Using an imaging window (sample slab) has many advantages, including flattening the surface of the skin at the point of measurement and allowing for higher reflectivity at the window/skin interface. However, it also gives rise to the presence of a baseline terahertz waveform, which is reflected from the first air/window boundary and is superimposed with the desired time-domain signal from the second interface with the skin. In order to remove the effect of the baseline interference, we used reference reflection measurements from a 3.175 mm thick fused silica slab. The reflection from this thicker slab was then aligned with and subtracted from the terahertz signal reflected from the thinner window and air boundary, in the time-domain, to give a "Differential Reference." Similarly, the thicker window reference was aligned with and subtracted from all subsequent normal and burned skin measurements.

Self calibration and signal processing: Before employing the Fast Fourier Transform (FFT) to investigate the spectral dependence of normal and burned skin samples, a split cosine taper was multiplied by the first and last 20 to 25 points of the time series and additional zeros were padded to both ends. The FFT amplitudes of the samples were normalized by the FFT of the differential reference to eliminate the effect of the intrinsic system response function. Moreover, to account for a typical terahertz signal amplitude drift in between measurements, the signal peak from the first interface of the slab, between air and fused silica, was used to self-calibrate each measurement with that of the references[30].

FIG. 1 shows histological sections of Hematoxylin and Eosin (H&E) stained biopsy samples for several groups of $2^{nd}$ and $3^{rd}$ degree burns created with this protocol. Biopsy samples were blindly studied by histopathologists, confirming the existence of $2^{nd}$ and $3^{rd}$ degree burns, as appropriate, in every sample generated by this protocol. Nonetheless, these images show that even when the same physical protocol is used to create burns, a wide range of damage can result. This variation is mostly due to the random fluctuation of the number and size of normal skin constituents such as hair follicles, sweat glands, capillaries, etc. Most notably we have observed three groups of skin burns, as represented in the columns of FIG. 1, based on the skin structures present after generation of $2^{nd}$ and $3^{rd}$ degree injuries. In the first column, a deep coagulated layer of the burned tissue was identified with few superficial cracks, while in the second column, a number of hair follicles and sweat ducts can be seen in the burned regions of the dermis.

Terahertz time-domain spectroscopy measurements of burned and healthy control tissue were obtained using a self-calibrating technique through a fused silica imaging window. The reflection measurements were obtained immediately and 72 hours post burn at an angle of incidence close to normal ($\theta<10°$). The 72 hour juncture was chosen based on the peak of the standard inflammatory reaction of the tissue to thermal damage by formation of interstitial edema. Due to the inhomogeneity of skin tissue, and especially because the size of normal skin structures are comparable to the terahertz wavelength, for each skin sample the average reflectivity over several (3-5) spatially disjoint terahertz realizations was obtained. Moreover, the spot size of the beam was approximately 2 mm in diameter at the focal point. FIG. 2(a,b) shows the normalized excess terahertz reflectivity of burns, induced with either 100° C. for 3 seconds or 100° C. for 30 seconds protocol, immediately and 72 hours post injury. The error bars show the full range of the data obtained over different rats participating in the study. The progression of the burn injuries can be seen by comparison between the acute and 72-hours characterization of the wounds. It is evident that the large degree of variability between samples renders the simple use of the percentage change in the THz reflectivity relative to healthy (control) tissue too ineffectual for the discrimination of burn severity.

This observation is in part because burn wounds are not static in their physiological nature[2, 9, 35]. For example, as explained earlier, some of the $2^{nd}$ degree injuries can reach a full-thickness ($3^{rd}$ degree) within a few days, due to the extent of thermal damage to the microvasculature and epithelium generation sites. This dynamic nature of the wound further complicates burn triage at the time of patient presentation.

Density of skin structures: Histopathological study of wound biopsies remains the gold standard of the burn depth assessment despite its invasive and time-consuming nature. Even though there still does not exist any universally accepted benchmark for inference of burn depth from histological sections[36], the accuracy of all other technological aids are usually measured against this method. The complexity of the dynamic molecular and cellular level changes, which skin constituents experience post burn, gives rise to most of the discrepancies in this field. For instance, while some studies indicate that the patency of microvasculature at the burn sites is the most critical factor in recovery[36], other methods emphasize cellular and epithelial intactness as the main predictor for wound healing. The presence of discrete skin structures, which are also known to be determinants of the healing likelihood of the burned skin[11-12, 34, 36], can potentially give rise to scattering of electromagnetic waves as they propagate through skin layers. In this section, we introduce a simple image processing method to objectively quantify the density of skin structures (DOS) in an attempt to relate our histopathological findings to the THz observations.

Figure 3:
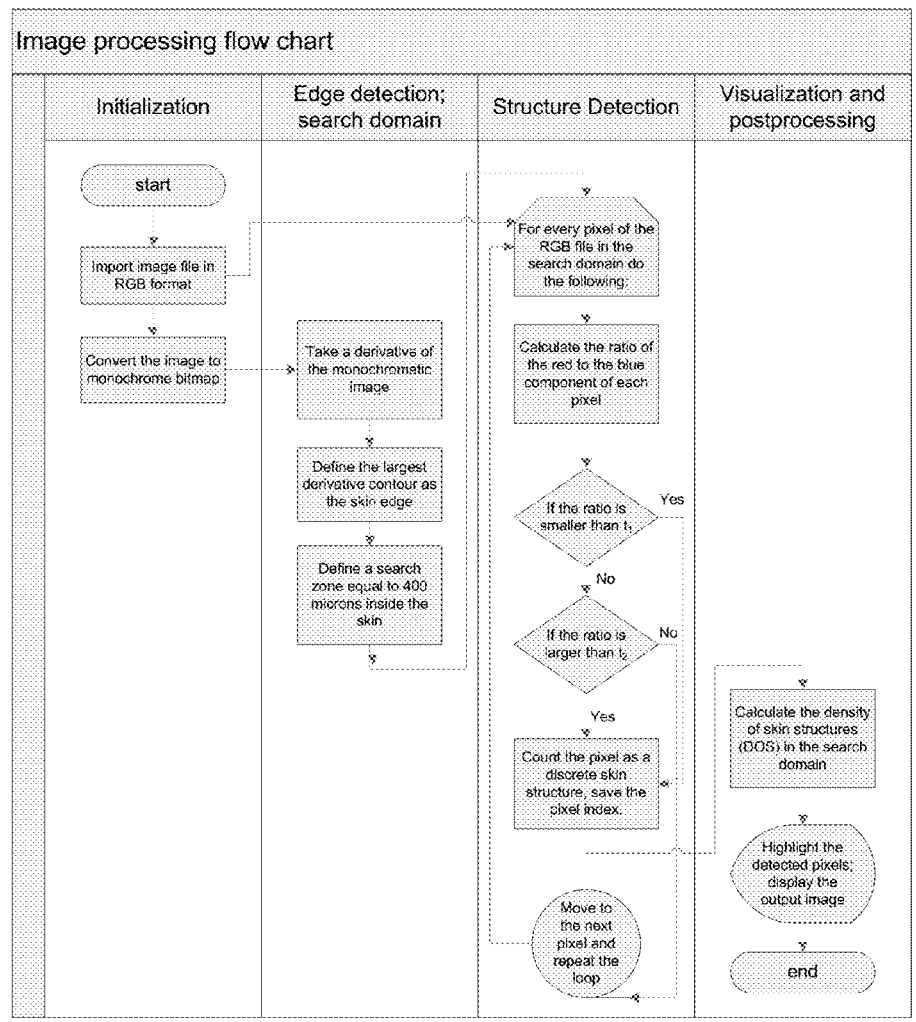
FIG. 3. (a) Cross-functional flow chart of the image processing and DOS calculation routine. The thresholds $t_1$ and $t_2$ are determined through optimization and learning algorithms. (b-c) typical output figures of the burned skin sections after the image processing algorithm, for a representative $3^{rd}$ and $2^{nd}$ degree burn respectively.

FIG. 3(a) shows a flowchart diagram of the steps involved in the image processing of the histology sections to count each pixel associated with the discrete structures in the burned and normal skin samples. The algorithm first identifies the skin edge and subsequently defines a search area approximately 400 μm deep in the tissue. It then recognizes tissue structures such as microvascular capillaries, hair follicles, sweat glands, and their skin duct based on the ratio of the red and blue components of the acquired image. Finally, the program calculates the total areal density of such structures within the search area. This density value is the largest (~20-30%) for healthy skin, and the more severely the tissue is damaged, the smaller the DOS will be. FIG. 3(b-c) shows typical outcomes of the image processing routine for both normal and burn samples.

FIG. 4 maps out our experimental results in the form of a scatter plot, where the x-axis shows the average reflectivity of skin samples between 0.2 and 1 THz, while the y-axis shows the spectral slope or rate of change in reflectivity with respect to frequency at 72 hours post injury. The color code is determined by the DOS metric from the image processing analysis. The symbols used designate each rat in our study and can be used to identify the normal tissue (control) for each burn. The dashed y=−x lines, which are offset for clarity, are drawn here as a visual aid. It can be seen that while all normal samples are aggregated in the lower left quadrant of the figure, the burned tissue data are spread out according to the degree of deviation of the THz reflectivity from their respective normal controls. In this plot, the excess reflectivity along the x-axis is generally attributed to the formation of interstitial edema at the burned sites [30-33]. However, the change in the spectral slope of the THz reflectivity (THz color of the burns), which is shown in the y-axis, is not well understood. One possible explanation suggests that a potential change in the dispersive properties of normal tissue as a result of thermal injury can be responsible for this observation. It may also be consistent with a reduction in electromagnetic scattering of terahertz waves due to a decrease in the density of discrete scatterers, i.e. the DOS value, as we observe here. Specifically, in all normal tissue samples, where the DOS is the largest, the normalized THz reflectivity showed a steep roll-off with higher frequencies, resulting in negative slope values along the y-axis for the blue symbols in FIG. 4. However, the burned samples demonstrated near-zero or positive spectral slopes, suggesting reduced scattering levels as the DOS value decreases.

From this map, we infer that some of the $2^{nd}$ degree injuries were severe enough to reach DOS values of $3^{rd}$ degree burns within 72 hours. For example in FIG. 4, the burn sample marked with DOS=6.7% was created with a $2^{nd}$ degree protocol, but in both THz spectroscopy response and DOS it has reached values corresponding to a full-thickness burn. We can also hypothesize from histology that other samples had begun to heal within the same period. For instance, the $2^{nd}$ degree burn with DOS estimated at 15%, placed very closely to its normal control tissue on the scatter plot, illustrate this effect. Of the 9 rats in our survival studies, we found only one outlier to this general trend (a nominally $2^{nd}$ degree burn with DOS value of 7.7%).

Figure 5:
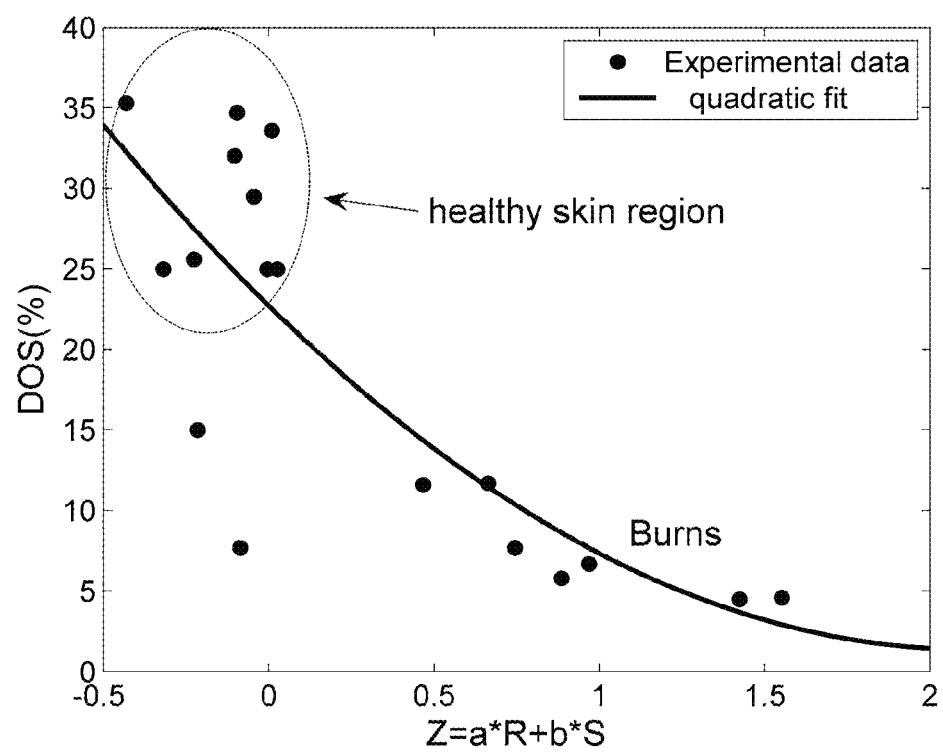
FIG. 5. The anti-correlation between the DOS and Z metrics (after optimization of a and b coefficients) are shown.

These results suggest that while discrimination of burn severity cannot be ascertained solely based on the absolute value of the terahertz reflectivity, a combined measure of reflectivity (R) and spectral slope (S) can differentiate among them based on the DOS metric. We define this combined measure, Z, with a linear combination of R and S, as given in Eq. (1), $$Z = a \cdot R + b \cdot S \quad (1)$$

where $0 < a$ and $b \leq 1$ are two arbitrary coefficients that can be optimized to achieve the maximum specificity in Z for differentiation of burn grades. The results of our optimization search over all experimental results reveal that all a=b contours satisfy such a condition. FIG. 5 summarizes our hypothesis for a new burn diagnosis criterion using this combined measure, Z, when a=b=1. Specifically, we hypothesize that the anti-correlation relation between DOS and Z, as shown in FIG. 5, can be used to infer the severity of burn injuries, and therefore their likelihood for spontaneous healing, when THz radiation is used to interrogate the intactness of skin structures.

We have presented experimental results from in vivo terahertz time-domain spectroscopy of $2^{nd}$ and $3^{rd}$ degree burns in a survival study over the 72 hour period post injury. We showed examples of the wide range of histopathological manifestation of burn tissue that must be characterized during triage for successful treatment of burns. We then introduced an image processing approach to objectively quantify the severity of these injuries based on the DOS metric. We showed that the terahertz response of different burn grades is not only consistent with the presumed overall water content in the tissue, but also correlates with the density of discrete scattering structures within the skin layers. These observations suggest, in turn, a new diagnosis criterion for clinical discrimination of burn injuries based on the THz response of the tissue.

REFERENCES

1. E. Mandelcorn, M. Gomez and R. C. Cartotto, "Work-related burn injuries in Ontario, Canada: Has anything changed in the last 10 years?," Burns 29 (5), 469-472 (2003).
2. B. S. Atiyeh, S. W. Gunn and S. N. Hayek, "State of the art in burn treatment," World J. Surg. 29 (2), 131-148 (2005).
3. J. M. Still, E. J. Law, K. G. Klavuhn, T. C. Island and J. Z. Holtz, "Diagnosis of burn depth using laser-induced Indocyanine green fluorescence: A preliminary clinical trial," Burns 27 (4), 364-371 (2001).
4. P. Shakespeare, "Burn wound healing and skin substitutes," Burns 27 (5), 517-522 (2001).
5. M. A. Afromowitz, J. B. Callis, D. M. Heimbach, L. A. DeSoto and M. K. Norton, "Multispectral imaging of burn wounds: A new clinical instrument for evaluating burn depth," IEEE Trans. Biomed. Eng. 35 (10), 842-850 (1988).
6. H. A. Green, D. Bua, R. R. Anderson and N. S. Nishioka, "Burn depth estimation using Indocyanine green fluorescence," Arch. Dermatol. 128 (1), 43-49 (1992).
7. M. J. Koruda, A. Zimbler, R. G. Settle, D. O. Jacobs, R. H. Rolandelli, G. L. Wolf and J. L. Rombeau, "Assessing burn wound depth using in vitro nuclear magnetic resonance (NMR)," J. Surg. Res. 40 (5), 475-481 (1986).
8. S. Iraniha, M. E. Cinat, V. M. VanderKam, A. Boyko, D. Lee, J. Jones and B. M. Achauer, "Determination of burn depth with noncontact ultrasonography," J. Burn Care Res. 21 (4), 333-338 (2000).
9. A. Papp, T. Lahtinen, M. Harma, J. Nuutinen, A. Uusaro and E. Alhava, "Dielectric Measurement in Experimental Burns: A New Tool for Burn Depth Determination?," Plast. Reconstr. Surg. 117 (3), 889-898 (2006).
10. A. D. Jaskille, J. C. Ramella-Roman, J. W. Shupp, M. H. Jordan and J. C. Jeng, "Critical review of burn depth assessment techniques: part II. Review of laser Doppler technology," J. Burn Care Res. 31(1), 151-157 (2010).
11. S. M. Srinivas, J. F. Boer, H. Park, K. Keikhanzadeh, H.-e. L. Huang, J. Zhang, W. Q. Jung, Z. Chen and J. S. Nelson, "Determination of burn depth by polarization-sensitive optical coherence tomography," J. Biomed. Opt. 9 (1), 207-212 (2004).
12. M. G. Sowa, L. Leonardi, J. R. Payette, K. M. Cross, M. Gomez and J. S. Fish, "Classification of burn injuries using near-infrared spectroscopy," J. Biomed. Opt. 11 (5), 054002 (2006).
13. K. M. Cross, L. Leonardi, J. R. Payette, M. Gomez, M. A. Levasseur, B. J. Schattka, M. G. Sowa and J. S. Fish, "Clinical utilization of near-infrared spectroscopy devices for burn depth assessment," Wound Repair Regen. 15 (3), 332-340 (2007).
14. P. H. Siegel, "Terahertz technology in biology and medicine," IEEE Trans. Microw. Theory Tech. 52 (10), 2438-2447 (2004).
15. E. Pickwell and V. P. Wallace, "Biomedical applications of terahertz technology," J. Phys. D Appl. Phys. 39 (17), R301 (2006).
16. D. B. Bennett, Z. D. Taylor, P. Tewari, R. S. Singh, M. O. Culjat, W. S. Grundfest, D. J. Sassoon, R. D. Johnson, J.-P. Hubschman and E. R. Brown, "Terahertz sensing in corneal tissues," J. Biomed. Opt. 16 (5), °, 7003 (2011).
17. Z. D. Taylor, R. S. Singh, D. B. Bennett, P. Tewari, C. P. Kealey, N. Bajwa, M. O. Culjat, A. Stojadinovic, L. Hua, J. P. Hubschman, E. R. Brown and W. S. Grundfest, "THz medical imaging: In vivo hydration sensing," IEEE Trans. Terahertz Sci. Technol. 1 (1), 201-219 (2011).
18. J. Federici, "Review of moisture and liquid detection and mapping using terahertz imaging," J. Infrared Milli. Terahz. Waves 33 (2), 97-126 (2012).
19. E. Pickwell, B. E. Cole, A. J. Fitzgerald, V. P. Wallace and M. Pepper, "Simulation of terahertz pulse propagation in biological systems," Appl. Phys. Lett. 84 (12), 2190-2192 (2004).
20. E. Pickwell, B. E. Cole, A. J. Fitzgerald, M. Pepper and V. P. Wallace, "In vivo study of human skin using pulsed terahertz radiation," Phys. Med. Biol. 49 (9), 1595 (2004).
21. J. T. Kindt and C. A. Schmuttenmaer, "Far-infrared dielectric properties of polar liquids probed by femtosecond terahertz pulse spectroscopy," J. Phys. Chem. 100 (24), 10373-10379 (1996).

22. R. M. Woodward, V. P. Wallace, R. J. Pye, B. E. Cole, D. D. Arnone, E. H. Linfield and M. Pepper, "Terahertz Pulse Imaging of ex vivo Basal Cell Carcinoma," *J. Investig. Dermatol.* 120 (1), 72-78 (2003).
23. V. P. Wallace, A. J. Fitzgerald, S. Shankar, N. Flanagan, R. Pye, J. Cluff and D. D. Arnone, "Terahertz pulsed imaging of basal cell carcinoma ex vivo and in vivo," *Br. J. Dermatol.* 151 (2), 424-432 (2004).
24. R. M. Woodward, B. E. Cole, V. P. Wallace, R. J. Pye, D. D. Arnone, E. H. Linfield and M. Pepper, "Terahertz pulse imaging in reflection geometry of human skin cancer and skin tissue," *Phys. Med. Biol.* 47 (21), 3853 (2002).
25. A. J. Fitzgerald, V. P. Wallace, M. Jimenez-Linan, L. Bobrow, R. J. Pye, A. D. Purushotham and D. D. Arnone, "Terahertz pulsed imaging of human breast tumors," *Radiology* 239 (2), 533-540 (2006).
26. P. C. Ashworth, E. Pickwell-MacPherson, E. Provenzano, S. E. Pinder, A. D. Purushotham, M. Pepper and V. P. Wallace, "Terahertz pulsed spectroscopy of freshly excised human breast cancer," *Opt. Express* 17 (15), 12444-12454 (2009).
27. V. P. Wallace, A. J. Fitzgerald, E. Pickwell, R. J. Pye, P. F. Taday, N. Flanagan and T. Ha, "Terahertz Pulsed Spectroscopy of Human Basal Cell Carcinoma," *Appl. Spectrosc.* 60 (10), 1127-1133 (2006).
28. D. M. Mittleman, M. Gupta, R. Neelamani, R. G. Baraniuk, J. V. Rudd and M. Koch, "Recent advances in terahertz imaging," *Appl. Phys. B* 68 (6), 1085-1094 (1999).
29. Z. D. Taylor, R. S. Singh, M. O. Culjat, J. Y. Suen, W. S. Grundfest, H. Lee and E. R. Brown, "Reflective terahertz imaging of porcine skin burns," *Opt. Lett.* 33 (11), 1258-1260 (2008).
30. M. H. Arbab, T. C. Dickey, D. P. Winebrenner, A. Chen, M. B. Klein and P. D. Mourad, "Terahertz reflectometry of burn wounds in a rat model," *Biomed. Opt. Express* 2 (8), 2339-2347 (2011).
31. P. Tewari, C. Kealey, J. Sung, A. Maccabi, N. Bajwa, R. Singh, M. Culjat, A. Stojadinovic, W. Grundfest and Z. D. Taylor, "Advances in biomedical imaging using THz technology with applications to burn-wound assessment," *Proc. SPIE* 8261, 82610T (2012).
32. P. Tewari, C. P. Kealey, D. B. Bennett, N. Bajwa, K. S. Barnett, R. S. Singh, M. O. Culjat, A. Stojadinovic, W. S. Grundfest and Z. D. Taylor, "In vivo terahertz imaging of rat skin burns," *J. Biomed. Opt.* 17 (4), 040503 (2012).
33. M. H. Arbab, T. C. Dickey, D. P. Winebrenner, A. Chen and P. D. Mourad, "Characterization of burn injuries using terahertz time-domain spectroscopy," *Proc. SPIE* 7890, 78900Q (2011).
34. T. W. Panke and C. G. McLeold, *Pathology of Thermal Injury: a Practical Approach*. Grune & Stratton, Orlando, Fla. (1985).
35. D. J. McGill, K. Sorensen, I. R. MacKay, I. Taggart and S. B. Watson, "Assessment of burn depth: A prospective, blinded comparison of laser Doppler imaging and videomicroscopy," *Burns* 33 (7), 833-842 (2007).
36. A. M. I. Watts, M. P. H. Tyler, M. E. Perry, A. H. N. Roberts and D. A. McGrouther, "Burn depth and its histological measurement," *Burns* 27 (2), 154-160 (2001).

We claim:

1. A method for assessing a burn injury, comprising:
   (a) acquiring reflectivity measurements of burned tissue of a subject, wherein the reflectivity measurements are generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;
   (b) determining a rate of change in the reflectivity measurements between different frequencies at one of the one or more appropriate times post-burn; and
   (c) determining a severity of the burn injury based on the rate of change.

2. The method of claim 1, wherein the acquiring comprises use of THz time domain spectroscopy (THz-TDS).

3. The method of claim 1, wherein the reflectivity measurements are normalized to limit effect of drift of a device used to generate the radiation.

4. The method of claim 1, wherein each reflectivity measurement comprises an average of several spatially disjointed reflectivity measurements for the respective frequency corresponding to that reflectivity measurement.

5. The method of claim 1, wherein the plurality of frequencies comprises frequencies at least between about 0.01 THz and about 10 THz.

6. The method of claim 1, wherein the plurality of frequencies comprises at least three different frequencies.

7. The method of claim 1, wherein the plurality of frequencies comprises at least 100 different frequencies.

8. The method of claim 1, wherein the one or more appropriate times post-burn comprise one or more times between immediately after burn injury to about 14 days post-burn.

9. The method of claim 1, wherein the determining severity of the burn injury comprises one or both of:
   (a) determining whether the burn injury is a full thickness burn or a partial thickness burn; and
   (b) determining whether the burn injury is likely to require surgical intervention or is likely to heal without surgical intervention.

10. The method of claim 1, where the method further comprises treating the burn injury based on the determined severity of the burn injury.

11. The method of claim 1, wherein the plurality of frequencies comprises frequencies at least between about 0.2 THz and about 1 THz.

12. The method of claim 1, wherein acquiring reflectivity measurements of burned tissue of a subject comprises exposing the subject to the plurality of radiation frequencies at a single time.

13. The method of claim 1, wherein determining the severity of the burn injury based on the rate of change comprises comparing the rate of change to previously determined rates of change from subjects with full thickness burns, partial thickness burns, and/or non-burned skin.

14. The method of any one of claim 1, wherein the reflectivity measurements are acquired by a THz spectroscope, the method further comprising:
   (a) acquiring a sample-reference THz reflection signal from an air-sample reference slab interface;
   (b) for a sample reflectivity measurement taken on the THz spectroscope using the sample slab, acquiring a sample THz reflection signal from an air-sample slab interface, wherein the sample slab has the same thickness as the sample-reference slab; and
   (c) determining a corrected sample reflectivity measurement based on a difference between the sample THz reflection signal and the sample-reference THz reflection signal.

15. The method of claim 14, further comprising:
   (a) acquiring a baseline-reference THz reflection signal from an air-baseline reference slab interface, wherein the baseline reference slab and the sample reference slab comprise the same material, wherein the baseline reference slab is at least twice as thick as the sample reference slab, and wherein the THz spectroscope includes a sample slab comprising the same material and having the same thickness as the sample reference slab;
(b) determining a difference between the sample-reference THz reflection signal and the baseline-reference THz reflection signal to produce a differential THz reflection signal;
(c) determining a difference between the corrected sample reflectivity measurement and the baseline-reference THz reflection signal to produce a baseline-removed corrected sample reflectivity measurement;
(d) taking a Fourier transform of (i) the differential THz reflection signal and (ii) the baseline-removed corrected sample reflectivity measurement; and
(e) determining a final corrected sample reflectivity measurement, wherein determining the final corrected sample reflectivity measurement comprises dividing the Fourier transform of the baseline-removed corrected sample reflectivity measurement by the Fourier transform of the differential THz reflection signal.

16. A computer-implemented method, comprising:
(a) receiving reflectivity-measurement data including at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;
(b) determining a rate of change in the reflectivity measurement between different frequencies at one of the one or more appropriate times post-burn;
(c) determining a severity of the burn injury based on the rate of change; and
(d) causing an indication of the determined severity of the burn injury to be displayed on a graphical display.

17. A computing device, comprising:
at least one processor;
a nontransitory computer readable medium; and
program data and logic stored on the nontransitory computer readable medium, which when executed by the at least one processor cause the computing device to:
(a) receive reflectivity-measured data indicating at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;
(b) determine a rate of change in the reflectivity measurements between different frequencies at one of the one or more appropriate times post-burn;
(c) determine a severity of the burn injury based on the rate of change; and
(d) cause an indication of the determined severity of the burn injury to be displayed on a graphical display.

18. A nontransitory computer-readable medium having computer executable instructions stored thereon, the instructions comprising:
(a) instructions for receiving reflectivity-measurement data indicating at least one reflectivity measurement of a burned tissue of a subject, wherein the reflectivity data is generated at one or more appropriate times post-burn by exposure of the burned tissue to radiation, the radiation comprising a plurality of frequencies at least between about 0.001 THz and about 30 THz, and wherein each reflectivity measurement corresponds to a respective frequency from the plurality of frequencies;
(b) instructions for determining a rate of change in the reflectivity measurements between different frequencies at one of the one or more appropriate times post-burn;
(c) instructions for determining a severity of the burn injury based on the rate of change; and
(d) instructions for causing an indication of the determined severity of the burn injury to be displayed on a graphical display.

* * * * *